United States Patent
Zhang (10) Patent No.: US 8,529,767 B2
(45) Date of Patent: Sep. 10, 2013

(54) METHOD FOR DETERMINING THE PERCENTAGE OF RECIRCULATION IN A FISTULA AND/OR CARDIOPULMONARY RECIRCULATION RELATIVE TO THE TOTAL FISTULA RECIRCULATION AND CARDIOPULMONARY RECIRCULATION

(75) Inventor: Wei Zhang, Niederwerrn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 216 days.

(21) Appl. No.: 12/812,261

(22) PCT Filed: Jan. 8, 2009

(86) PCT No.: PCT/EP2009/000054
§ 371 (c)(1),
(2), (4) Date: Jul. 9, 2010

(87) PCT Pub. No.: WO2009/087092
PCT Pub. Date: Jul. 16, 2009

(65) Prior Publication Data
US 2010/0276367 A1    Nov. 4, 2010

(30) Foreign Application Priority Data
Jan. 9, 2008  (DE) .......................... 10 2008 003 714

(51) Int. Cl.
*B01D 11/00* (2006.01)
*B01D 61/00* (2006.01)
*C02F 1/44* (2006.01)

(52) U.S. Cl.
USPC .......... 210/647; 210/96.2; 210/646; 210/739; 604/5.01; 604/6.09; 604/6.13

(58) Field of Classification Search
None
See application file for complete search history.

(56) References Cited

U.S. PATENT DOCUMENTS

| 4,267,040 | A | 5/1981 | Schal |
| 4,702,829 | A | 10/1987 | Polaschegg et al. |

(Continued)

FOREIGN PATENT DOCUMENTS

| DE | 19528907 C1 | 11/1996 |
| DE | 19541783 C1 | 3/1997 |

(Continued)

OTHER PUBLICATIONS

M. Kramer and HD. Polaschegg, "Automated measurement of recirculation", EDTNA-ERCA Journal 19, No. 2, p. 6-9. (Apr. 1993).

(Continued)

*Primary Examiner* — Dirk Bass
(74) *Attorney, Agent, or Firm* — Kenyon & Kenyon LLP (57) ABSTRACT

The method according to the invention and the apparatus according to the invention are characterized in that the substitution rate $Q_S$ is modified by a predefined amount upstream or downstream of the dialyzer or filter while the flow rate $Q_{FM}$ of the liquid withdrawn through the dialyzer membrane is modified. The blood volume RBV(t) or a variable correlated with the blood volume, e.g. the hematocrit Hct(t), is determined before and after modifying the substitution rate or the flow rate of the liquid withdrawn through the dialyzer or filter membrane in order to calculate fistula recirculation $R_A$. In addition, the total recirculation R is determined. The percentage of fistula recirculation ($R_A$) and/or cardiopulmonary recirculation ($R_{CP}$) relative to the total recirculation is calculated from the determined fistula recirculation ($R_A$) and the sum R of fistula recirculation ($R_A$) and cardiopulmonary recirculation ($R_{CP}$).

11 Claims, 2 Drawing Sheets

(56) References Cited

U.S. PATENT DOCUMENTS

| | | | |
|---|---|---|---|
| 5,830,365 A | 11/1998 | Schneditz | |
| 5,866,015 A | 2/1999 | Kramer | |
| 6,537,240 B2 | 3/2003 | Cavicchioli et al. | |
| 7,001,353 B2 | 2/2006 | Bosetto et al. | |
| 7,341,568 B2 | 3/2008 | Zhang | |
| 7,704,213 B2 | 4/2010 | Kraemer | |
| 2004/0073153 A1* | 4/2004 | Bosetto et al. | 604/5.03 |
| 2006/0047193 A1 | 3/2006 | Zhang | |
| 2006/0064025 A1 | 3/2006 | Kraemer | |
| 2006/0200064 A1* | 9/2006 | Gross et al. | 604/5.01 |
| 2006/0254982 A1 | 11/2006 | Kopperschmidt | |

FOREIGN PATENT DOCUMENTS

| | | |
|---|---|---|
| DE | 19702441 C1 | 2/1998 |
| DE | 10230413 A1 | 1/2004 |
| DE | 10259437 B3 | 9/2004 |
| EP | 0189561 A | 8/1986 |
| EP | 1595560 A1 | 11/2005 |
| JP | 63294866 A | 12/1988 |
| WO | 01/45770 A | 6/2001 |
| WO | 2006/072271 A | 7/2006 |

OTHER PUBLICATIONS

International Search Report, PCT/EP2009/000054, mailed Jun. 3, 2009.

D. Schneditz et al.: Cardiopulmonary recirculation during haemodialysis. Kidney Int. 42: 1450-1456, 1992.

W. Bay et al.: Color Doppler flow predicts PTFE graft failure, J. Am. Soc. Nephrol. 5: 407 (1994).

F. Gotch: "Models to predict recirculation and its effects on treatment time in single-needle-dialysis", First Intl. Symposium on Single-Needle-Dialysis, publisher: S. Rignoir, R. Vanholder and P. Ivanovich, Cleveland, ISAO Press, 1984, p. 305 ff.

* cited by examiner

METHOD FOR DETERMINING THE PERCENTAGE OF RECIRCULATION IN A FISTULA AND/OR CARDIOPULMONARY RECIRCULATION RELATIVE TO THE TOTAL FISTULA RECIRCULATION AND CARDIOPULMONARY RECIRCULATION

CROSS REFERENCE TO RELATED APPLICATIONS

This is a 371 national phase application of PCT/EP2009/000054 filed Jan. 8, 2009, claiming priority to German Patent Application No. 10 2008 003 714.1 filed Jan. 9, 2008.

FIELD OF INVENTION

The invention relates to a method for determining the share of the recirculation in a fistula and/or the cardiopulmonary recirculation in the sum of fistula recirculation and cardiopulmonary recirculation for an extracorporeal blood treatment with an extracorporeal blood circuit, which includes a first chamber of a dialyzer or filter divided by a membrane into the first chamber and a second chamber, and a fluid system which includes the second chamber of the dialyzer or filter, blood being fed at a specific blood flow rate to the first chamber of the dialyzer or filter and substitution fluid being fed at a specific substitution rate to the blood upstream or downstream of the first chamber of the dialyzer or filter and fluid being withdrawn at a specific flow rate from the blood via the membrane of the dialyzer or filter.

Furthermore, the invention relates to a device for determining the share of the fistula recirculation and/or the cardiopulmonary recirculation in the sum of fistula recirculation and cardiopulmonary recirculation for an apparatus for extracorporeal blood treatment. Moreover, the invention relates to an extracorporeal blood treatment apparatus with a device for determining the share of the fistula recirculation and/or the cardiopulmonary recirculation in the sum of fistula and cardiopulmonary recirculation.

BACKGROUND OF THE INVENTION

For the purpose of removing substances usually eliminated with urine and for the purpose of withdrawing fluid, use is made of various methods for extracorporeal blood treatment and cleaning. In the case of hemodialysis, the patient's blood is cleaned outside the body in a dialyzer. The dialyzer comprises a blood chamber and a dialyzing fluid chamber, which are separated by a semipermeable membrane. During the treatment, the patient's blood flows through the blood chamber. In order to clean the blood effectively from substances usually eliminated with urine, fresh dialyzing fluid continuously flows through the dialyzing fluid chamber.

Whereas the transport of the smaller molecular substances through the membrane of the dialyzer is essentially determined in the case of hemodialysis (HD) by the concentration differences (diffusion) between the dialyzing fluid and the blood, substances dissolved in the plasma water, in particular higher molecular substances, are effectively removed in the case of the hemofiltration (HF) by a high fluid flow (convection) through the membrane of the dialyzer. The dialyzer acts as a filter in hemofiltration. Hemodiafiltration (HDF) is a combination of the two methods.

In the case of hemo(dia)filtration, a part of the fluid withdrawn from the blood through the membrane of the dialyzer is replaced by a sterile substitution fluid, which is generally fed to the extracorporeal blood circuit either upstream of the dialyzer or downstream of the dialyzer. The supply of the substitution fluid upstream of the dialyzer is also referred to as predilution and the supply downstream of the dialyzer as postdilution.

Apparatuses for hemo(dia)filtration are known in which the dialyzing fluid is prepared online from fresh water and dialyzing fluid concentrate and the substitution fluid is prepared online from the dialyzing fluid.

In the case of the known hemo(dia)filtration apparatuses, the substitution fluid (substituate) is fed to the extracorporeal blood circuit from the fluid system of the machine via a substituate supply line. In the case of predilution, the substituate line leads to a junction point on the arterial blood line upstream of the dialyzer or filter, whereas in the case of postdilution the substituate line leads to a junction point on the venous blood line downstream of the dialyzer or filter. The substituate line comprises for example a connector, with which it can be connected either to the venous or arterial blood line. In order to interrupt the fluid supply, a clamp or the like is provided on the substituate line. Such a hemo(dia)filtration apparatus is known for example from EP-A-0 189 561.

In the known methods of chronic blood-cleaning therapy, for example hemodialysis, hemofiltration and hemodiafiltration, an arteriovenous fistula is often applied surgically as an access to the blood vessel system. The use of an implant is also possible. When mention is made below of a "fistula", this is understood to mean any kind of connection between a vein and an artery of the patient.

The blood flowing through the fistula is used only during the actual dialysis treatment. In the period free from dialysis, the blood flow in the fistula corresponds to a functional left/right shunt, wherein a part of the arterial blood is fed from the heart minute volume (HMV), bypassing a peripheral use, directly to the venous system and the heart. The fistula flow recirculates via the heart and lungs. The functional part of the fistula flow in the heart minute volume is defined as the cardiopulmonary recirculation.

The cardiopulmonary recirculation not only has effects on the patient's circulatory load, but also on the efficiency of the dialysis. Since the dialyzed blood from the extracorporeal circuit is mixed with the venous backflow from the large body circulation thereby bypassing the systemic circulatory areas, a systematic reduction in the concentration of the dialyzable constituents in the arterial blood results (D. Schneditz et al.: Cardiopulmonary recirculation during hemodialysis. Kidney Int. 42: 1450-1456, 1992).

Of importance for the functional capability of fistulas is their perfusion. If the fistula flow falls below a critical value, the risk of a fistula thrombosis then increases with the possible loss of the vascular access, which in dialysis treatment represents a considerable complication (W. Bay et al.: Color Doppler flow predicts PTFE graft failure, J. Am. Soc. Nephrol. 5: 407 (1994)). If the fistula flow during the dialysis treatment is smaller than the extracorporeal blood flow($Q_B$), local fistula recirculation occurs, whereby a fraction of the dialysed blood fed back to the fistula with the venous blood line is again fed to the dialyzer via the arterial blood line. Fistula recirculation $R_A$ causes a significant reduction in the dialysis efficiency (F. Gotch: "Models to predict recirculation and its effects on treatment time in single-needle-dialysis", First Intl. Symposium on Single-Needle-Dialysis, publisher: S. Rignoir, R. Vanholder and P. Ivanovich, Cleveland, ISAO Press, 1984, page 305 ff.). The measurement of the quality of the vascular access is therefore an important means of quality assurance in dialysis treatment.

On account of its clinical importance, various methods are known for measuring the fistula recirculation ($R_A$). Common to all of them is the measurement of a physical or chemical characteristic quantity of the blood, which is changed in the venous branch of the extracorporeal circuit. The physical or chemical characteristic quantity of the blood can be changed by a manual injection of an indicator or also indirectly via the dialyzer preparation unit.

A method for the measurement of recirculation referred to as thermodilution is known from EDTNA-ERCA Journal 19, 6 (1993). With the known method, a brief drop in temperature is initiated in the dialyzing fluid circuit, which is transferred to the venous branch of the extracorporeal circuit and leads to a detectable temperature jump in the arterial branch of the extracorporeal circuit when a recirculation occurs.

A known device for performing the method referred to as thermodilution comprises a temperature sensor arranged in the arterial branch and one in the venous branch of the extracorporeal circuit. The venous temperature sensor is used to detect the temperature jump that is attributable to the drop in temperature produced in the dialyzing fluid circuit. The measured temperature jump is integrated over time or otherwise characterized and is subsequently compared with the temperature course recorded in the arterial measuring sensor. The ratio of the two temperature integrals or other characteristic quantities with respect to one another is a measure of the overall reduction in efficiency of the dialysis treatment due to fistula and cardiopulmonary recirculation.

The known device for the measurement of recirculation has been tried and tested in practice. It proves to be a drawback, however, that only the total recirculation denoted below as recirculation R can be measured, which corresponds to the sum of fistula recirculation $R_A$ and cardiopulmonary recirculation $R_{CP}$.

A method for measuring recirculation R, i.e. the sum of the fistula recirculation ($R_A$) and the cardiopulmonary recirculation ($R_{CP}$), is also known from DE 197 02 441 C1. With the known method, a physical or chemical characteristic quantity of the dialyzing fluid is changed in the dialyzing fluid path upstream of the dialyzer, which leads to a change in the physical or chemical characteristic quantity on the blood side. The change in the characteristic quantity of the dialyzing fluid on the blood side leads to a change in the characteristic quantity of the dialyzing fluid downstream of the dialyzing fluid chamber of the dialyzer. In order to determine the recirculation, the characteristic quantity is measured in the dialyzing fluid path downstream of the dialyzer and recirculation R is determined from the course of the change in the characteristic quantity as a function of time. As the physical or chemical characteristic quantity, the ion concentration of the dialyzing fluid, for example the Na concentration of the dialyzing fluid, or also the temperature of the dialyzing fluid can be changed and measured. The drawback, however, is once again that with the known method it is not possible to distinguish between fistula recirculation $R_A$ and cardiopulmonary recirculation $R_{CP}$.

DE-A-195 28 907 C1 describes a method for determining the cardiopulmonary recirculation. The measurement of the cardiopulmonary recirculation is based on two measurements of the recirculation fraction following one another in close succession, which are carried out automatically before and after the reversal of the blood flow. The drawback is that the known method requires the reversal of the blood flow.

A method for determining the recirculation is known from U.S. Pat. No. 6,537,240 B2, which is based on a change in the composition of the blood in the extracorporeal blood circuit due to an increase or reduction in the ultrafiltration rate within a predetermined time interval.

SUMMARY OF THE INVENTION

The problem underlying the invention is to provide a method which permits the determination of the share of the recirculation in a fistula and/or the cardiopulmonary recirculation in the sum of fistula recirculation and cardiopulmonary recirculation. Moreover, the problem of the invention is to make available a device for determining the share of the fistula recirculation and/or the cardiopulmonary recirculation in the sum of the fistula recirculation and cardiopulmonary recirculation. A further problem of the invention is to provide an extracorporeal blood treatment apparatus which comprises a device for determining the share of the fistula recirculation and/or the cardiopulmonary recirculation in the sum of the fistula and cardiopulmonary recirculation.

The method according to the invention and the device according to the invention for determining the share of the fistula recirculation and/or cardiopulmonary recirculation in the sum of fistula and cardiopulmonary recirculation, which is also referred to in the following as recirculation, requires an extracorporeal blood treatment in which substitution fluid is fed at a specific substitution rate to the blood upstream or downstream of the first chamber of the dialyzer or filter and fluid is withdrawn at a specific flow rate from the blood via the membrane of the dialyzer or filter. The method according to the invention and the device according to the invention are based on the fact that the substitution rate is changed by a predetermined amount upstream or downstream of the dialyzer or filter, whilst the flow rate of the fluid withdrawn through the membrane of the dialyzer is changed.

Before the change in the substitution rate or the flow rate of the fluid withdrawn through the membrane of the dialyzer or filter, blood volume $RBV(t_1)$ or a quantity correlating with the blood volume, for example hematocrit $Hct(t_1)$, the blood density or hemoglobin concentration, is determined. If the blood volume or the hematocrit is known before the change in the substitution rate or the flow rate of the fluid withdrawn through the membrane, the measurement of the blood volume or the hematocrit can be dispensed with.

After the change in the substitution rate or the flow rate of the fluid withdrawn through the membrane, the blood volume or the quantity correlating with the blood volume is again determined, in order to be able to detect the change in the blood volume or the quantity correlating with the blood volume as a result of the change in the substitution rate or the flow rate of the fluid withdrawn through the membrane. In principle, it is not necessary to determine the blood volume before and after the change in the flow rates as absolute quantities, but rather the determination of the change in the blood volume as a result of the change in the substitution rate or the flow rate of the fluid withdrawn through the membrane of the dialyzer is sufficient. For example, it is sufficient to determine the quotient of the relative blood volumes before and after the change in the flow rates.

Fistula recirculation $R_A$ is determined on the basis of the comparison of the blood volume or the quantity correlating with the blood volume before and after the change in the substitution rate and the flow rate of the fluid withdrawn through the membrane. The determination of fistula recirculation $R_A$ is thus possible solely on the basis of the change in the blood volume. Since the changed blood volume values are reached relatively quickly, the measurement of the fistula recirculation is distinguished by a relatively short measurement time, which can lie between 1 and 2 minutes in practice.

The effect of the relatively short measurement time is that only the share of the fistula recirculation, but not the share of the cardiopulmonary recirculation in recirculation R, i.e. the sum of fistula recirculation and cardiopulmonary recirculation, is detected. Since the cardiopulmonary recirculation occurs only after the lapse of the relatively short measurement time, this share of the recirculation is not detected.

In order to determine the share of fistula recirculation $R_A$ in total recirculation R, total recirculation R is ascertained according to the known methods. Recirculation R can be determined for example according to the method known as thermodilution (EDTNA-ERCA Journal 19, 6 (1993)). It is however also possible to determine the recirculation according to other known methods.

As soon as total recirculation R is determined, the share of fistula recirculation $R_A$ in total recirculation R and/or of cardiopulmonary recirculation $R_{CP}$ in total recirculation R is determined. Cardiopulmonary recirculation $R_{CP}$ can be calculated after the determination of fistula recirculation $R_A$ from the difference between total recirculation R and fistula recirculation $R_A$.

The method according to the invention and the device according to the invention are therefore essentially distinguished by the combination of a rapid determination of the fistula recirculation on the basis of a change in the substitution rate and the flow rate of the fluid withdrawn through the membrane of the dialyzer or filter and the determination of the sum of fistula recirculation and cardiopulmonary recirculation, in order to be able to ascertain the respective shares of fistula and cardiopulmonary recirculation in the total recirculation.

The determination of the fistula recirculation on the basis of the change in the substitution rate and the flow rate of the fluid withdrawn through the membrane is based on the fact that the change in these flow rates brings about a change in the density of the blood or the concentration of a blood constituent. There is formed in the extracorporeal blood circuit a kind of thickened or diluted "blood column" which represents a "bolus" limited in time, which recirculates in the fistula so quickly that it can be detected in the extracorporeal blood circuit before the slower cardiopulmonary recirculation starts. Consequently, the fistula recirculation, but not the cardiopulmonary recirculation, is detected with the relatively rapid measurement, so that, after the measurement of the sum of fistula and cardiopulmonary recirculation using the known measuring methods, the respective shares of fistula and/or cardiopulmonary recirculation in the recirculation can be determined. In principle, it is unimportant whether the blood volume or the quantity correlating with the blood volume, for example the hematocrit in the arterial or venous branch of the extracorporeal blood circuit, is determined, since the quantity in the venous or arterial branch of the extracorporeal circuit can be calculated after a measurement of this characteristic quantity in the arterial or venous branch.

A preferred embodiment of the method according to the invention and the device according to the invention provides for a reduction, by the same amount, of the substitution rate and the flow rate of the fluid withdrawn through the membrane of the dialyzer or filter.

In another embodiment, the supply of substitution fluid interrupted upstream or downstream of the dialyzer or filter and the withdrawal of fluid via the membrane of the dialyzer or filter are completely interrupted. The interruption preferably takes place for a predetermined time interval, so that the original conditions are restored after the lapse of the time interval.

In principle, however, it is also possible for the substitution rate and the flow rate of the fluid withdrawn through the membrane of the dialyzer or filter to be increased, preferably by the same amount, or for a supply of substitution fluid upstream or downstream of the dialyzer or filter and a withdrawal of fluid via the membrane of the dialyzer or filter to be carried out, the blood volume or the quantity correlating with the blood volume being measured beforehand and afterwards. Once again, there is the formation of a "blood column", the blood becoming diluted with postdilution and thickening with predilution.

The implementation of the method according to the invention in the known blood treatment apparatuses does not require a large outlay on equipment, since it is merely necessary to stop the substitution pump for a short time and to separate the dialyzer or filter from the extracorporeal blood circuit, so that fluid cannot be withdrawn via the membrane of the dialyzer or filter. For example, the measurement can be carried out together with the known pressure holding tests with blood treatment apparatuses in which the substitution pump is stopped and the dialyzer connected into a bypass.

An example of an embodiment of the blood treatment apparatus according to the invention is described in detail below by reference to the drawings, said apparatus comprising a device according to the invention for determining the share of the fistula recirculation and/or cardiopulmonary recirculation in the sum of the fistula and cardiopulmonary recirculation.

DETAILED DESCRIPTION OF THE DRAWINGS

Figure 1:
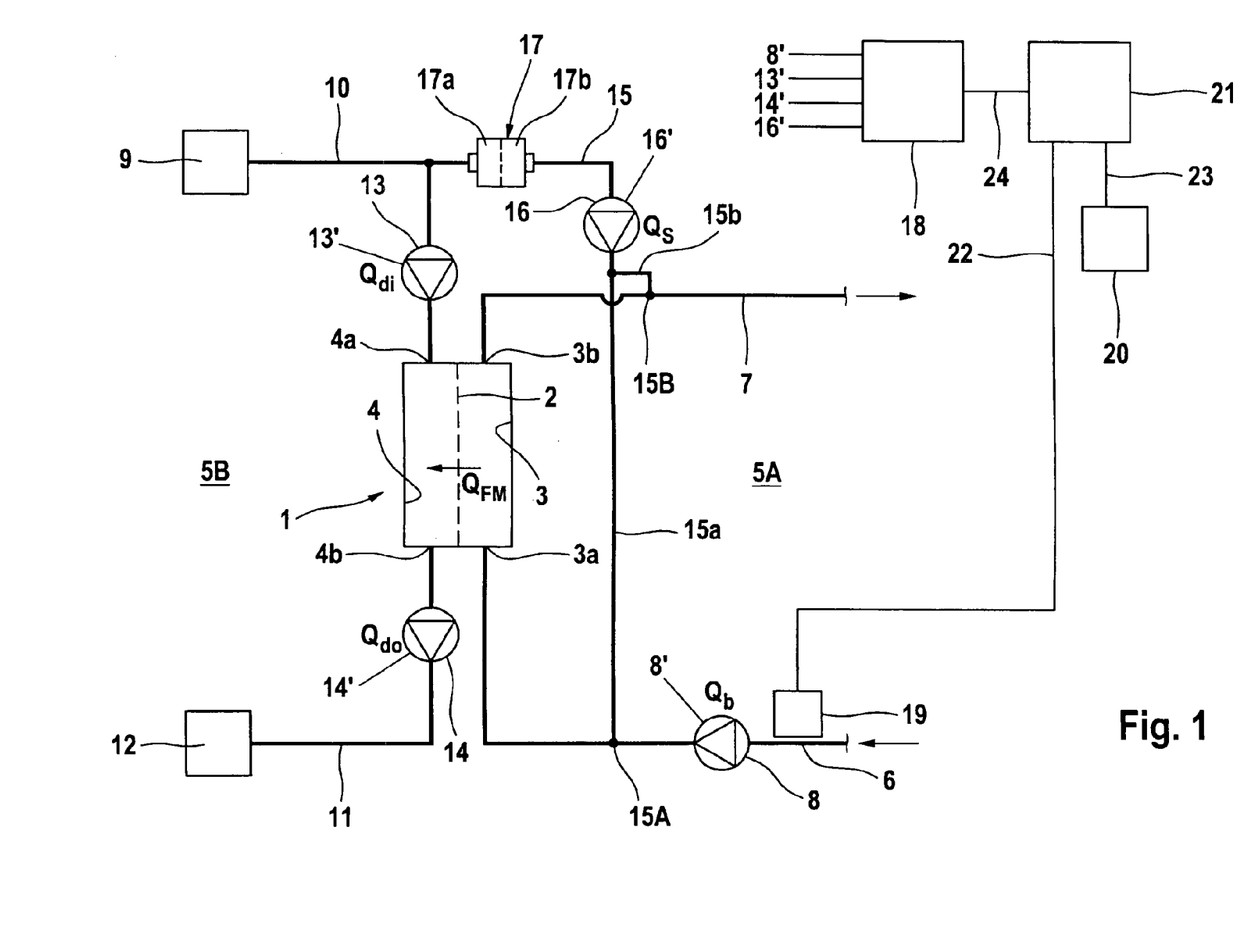
FIG. 1 shows an extracorporeal blood treatment apparatus with a device for determining the share of the fistula recirculation and/or the cardiopulmonary recirculation in the sum of the fistula and cardiopulmonary recirculation in a very simplified schematic representation.

FIG. 1 shows only the main components of the extracorporeal blood treatment apparatus in a schematic representation which are of relevance for the determination of the share of the fistula recirculation and/or the cardiopulmonary recirculation in the recirculation.

The present blood treatment apparatus is a hemo(dia)filtration apparatus, which comprises a dialyzer 1, which is separated by a semipermeable membrane 2 into a first chamber 3 through which blood flows, which is referred to in the following as a blood chamber, and a second chamber 4 through which dialyzing fluid flows, which is referred to as a dialyzer fluid chamber. First chamber 3 is incorporated into an extracorporeal blood circuit 5A, whilst second chamber 4 is incorporated into dialyzing fluid system 5B of the hemo (dia)filtration apparatus.

Extracorporeal blood circuit 5A comprises an arterial blood line 6, which leads to inlet 3a of chamber 3, and a venous blood line 7, which leads away from outlet 3b of chamber 3 of dialyzer 1. The patient's blood is delivered through blood chamber 3 of dialyzer 1 by an arterial blood pump 8, in particular a roller pump, which is disposed on arterial blood line 6. The blood pump feeds blood at a specific blood flow rate $Q_b$ to blood chamber 3 of the dialyzer. Blood lines 6, 7 and dialyzer 3 form a disposable unit intended for one-time use, which is inserted into the dialysis apparatus for the dialysis treatment. In order to eliminate air bubbles, air separators (drip chambers) can be incorporated into the arterial and venous blood line.

The fresh dialyzing fluid is prepared in a dialyzing fluid source 9. From dialyzing fluid source 9, a dialyzing fluid supply line 10 leads to inlet 4a of dialyzing fluid chamber 4 of dialyzer 1. A dialyzing fluid discharge line 11 leads from outlet 4b of dialyzing fluid chamber 4 to a drain 12. A first dialyzing fluid pump 13 is incorporated into dialyzing fluid supply line 10 and a second dialyzing fluid pump 14 is incorporated into dialyzing fluid discharge line 11. First dialyzing fluid pump 13 delivers dialyzing fluid from the dialyzing fluid source at a specific dialyzing fluid delivery rate $Q_{di}$ to inlet 4a of dialyzing fluid chamber 4, whilst second dialyzing fluid pump 14 delivers the dialyzing fluid at a specific dialyzing fluid discharge rate $Q_{do}$ from outlet 4b of dialyzing fluid chamber 4 to drain 12.

During the dialysis treatment, dialyzing fluid can be fed to extracorporeal blood circuit 5A from dialyzing fluid system 5B as substitution fluid via a substitution fluid line 15, which branches off from dialyzing fluid supply line 10 upstream of first dialyzing fluid pump 13. Substitution fluid line 15 comprises two line segments 15a and 15b, whereof one line segment 15a leads to arterial blood line 6 and other line segment 15b leads to venous blood line 7.

The substitution fluid is delivered by means of a substitution pump 16, in particular a roller pump, into which substitution fluid line 15 is inserted. A sterile filter 17 divided into two chambers 17a, 17b is incorporated into substitution fluid line 15 upstream of the substitution pump. The substitution pump together with the respective lines and the sterile filter form the substitution device of the dialysis apparatus. In order to clamp the two line segments 15a, 15b of substitution fluid line 15, shut-off elements, for example tube clamps, can be provided, which however are not represented for the sake of greater clarity.

Blood pump 8, first and second dialyzing fluid pumps 13 and 14 and substitution pump 16 are connected via control lines 8', 13', 14', 16' to a central control and regulation unit 18, from which the pumps are controlled taking account of the predetermined treatment parameters.

For the operation of the hemo(dia)filtration apparatus as a hemodialysis apparatus, blood pump 8 and first and second dialyzing fluid pumps 13 and 14 are operated, whereby dialyzing fluid flows through dialyzing fluid chamber 4 of dialyzer 1. For the operation of the hemo(dia)filtration apparatus as a hemodiafiltration apparatus, substitution pump 16 is operated, so that sterile dialyzing fluid as substitution fluid flows via sterile filter 17 optionally to arterial supply point 15A downstream of blood pump 8 and upstream of blood chamber 3 (predilution) or to venous supply point 15B downstream of the blood chamber (postdilution). Operation of the hemo(dia)filtration apparatus solely as a hemofiltration apparatus is however also possible if first dialyzing fluid pump 13 is not operated and thus the supply of dialyzing fluid into the dialyzing fluid chamber of the dialyzer is interrupted.

The device for determining the share of the fistula recirculation and/or the cardiopulmonary recirculation in the recirculation is a component of the extracorporeal blood treatment apparatus. The device comprises a control unit, which is a component of central control and computing unit 18 of the blood treatment apparatus.

Furthermore, the apparatus comprises a unit 19 for determining relative blood volume RBV(t) or a quantity correlating with the blood volume, for example hematocrit Hct(t). This unit is represented only schematically in FIG. 1, since devices for measuring the blood volume or hematocrit are known to the person skilled in the art. In principle, all known devices for measuring these quantities can be used. In the present example of embodiment, the relative blood volume or the hematocrit in the blood that is flowing through arterial blood line 6 is determined.

In addition, the apparatus comprises a unit 20 for determining the sum of fistula recirculation $R_A$ and cardiopulmonary recirculation $R_{CP}$. Such devices are also known to the person skilled in the art. For example, a device can be used which determines recirculation R according to the method known as thermodilution (EDTNA-ERCA Journal 19, 6 (1993)). In principle, however, all the other known devices for determining recirculation R can also be used.

The apparatus also comprises an evaluation unit 21, which is connected via data lines 22, 23 to unit 19 for determining the relative blood volume or hematocrit and to unit 20 for determining the recirculation. The evaluation unit communicates with central control unit 18 via a further data line 24.

During the extracorporeal blood treatment, control unit 18 controls blood pump 8 in such a way that blood flows at blood flow rate $Q_b$ into blood chamber 3 of dialyzer 1, and it controls first and second dialyzing fluid pumps 13, 14 in such a way that dialyzing fluid flows at dialyzing fluid rate $Q_{di}$ into dialyzing fluid chamber 4 and dialyzing fluid flows at dialyzing fluid rate $Q_{do}$ out of dialyzing fluid chamber 4. Control unit 18 controls substitution pump 16 in such a way that substitution fluid is fed at substitution rate $Q_S$ to the blood optionally upstream (predilution) and/or downstream (postdilution) of blood chamber 3.

The case of postdilution will next be described, wherein substitution pump 16 supplies substitution fluid at substitution rate $Q_S$ to the blood downstream of the blood chamber. In this case, the substitution fluid flows via line segment 15b of the substitution fluid line, while line segment 15a is shut off.

Figure 2:
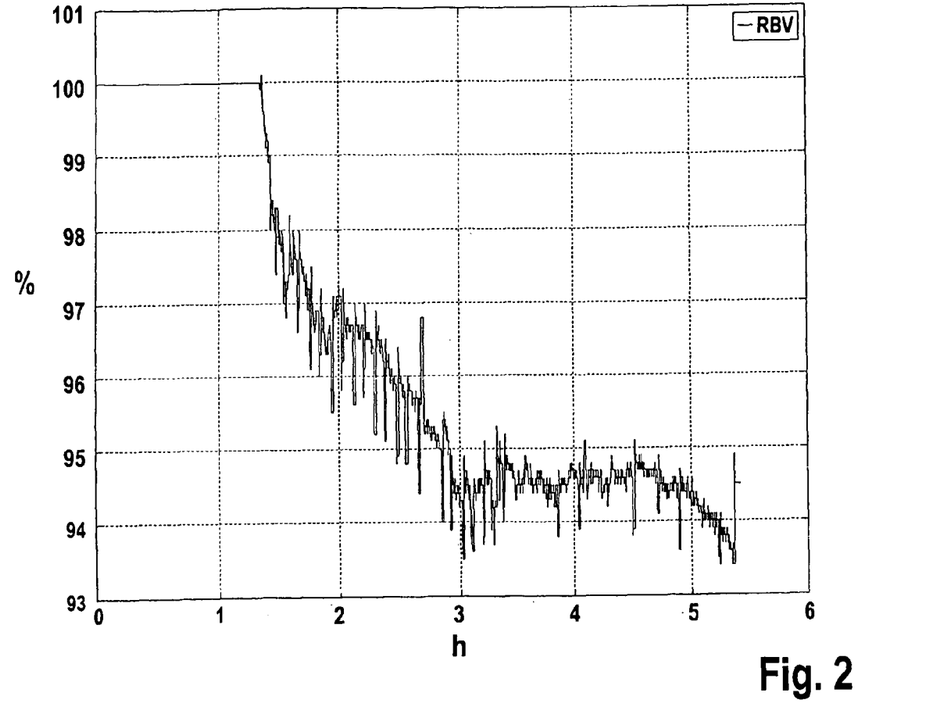
FIG. 2 shows the relative blood volume as a function of time during an extracorporeal blood treatment.

During the extracorporeal blood treatment, relative blood volume RBV(t) or hematocrit Hct(t) is continuously monitored by unit 19. FIG. 2 shows the course of the relative blood volume as a function of time during a blood treatment lasting several hours.

In order to determine the share of the fistula recirculation and/or the cardiopulmonary recirculation in the recirculation, control unit 18 controls substitution pump 16 in such a way that its delivery rate is preferably reduced by a predetermined amount preferably only for a predetermined time interval or substitution pump 16 is preferably stopped for a predetermined time interval. At the same time, control unit 18 controls first and second dialyzing fluid pumps 13 and 14 in such a way that flow rate $Q_{FM}$, i.e. the flow rate at which fluid is withdrawn from the extracorporeal blood circuit via the membrane of the dialyzer, is reduced within the same time interval by the same amount as the substitution rate is reduced, or the withdrawal of fluid via the membrane is completely interrupted within the same time interval. This can be brought about particularly easily with dialysis machines in which the function of the two dialyzing fluid pumps 13 and 14 is performed by a 1:1 balancing system and a separate ultrafiltration line, as is the case for example with the dialysis machine described in U.S. Pat. No. 4,267,040. In this case, substitution fluid line 15 branches off from dialyzing fluid supply line 10 preferably downstream of the balancing system. If the substitution pump is then switched off, there is also a corresponding reduction in the flow rate at which fluid is withdrawn from the extracorporeal blood circuit via the membrane of the dialyzer. If the dialyzer is then decoupled by means of a bypass (not shown) between the dialyzer supply line and dialyzer discharge line, any ultrafiltration in the dialyzer is prevented.

FIG. 2 shows the case where substitution pump 16 is switched off for a predetermined short time interval and at the same time first and second dialyzing fluid pumps 13, 14 are controlled in such a way that fluid (ultrafiltrate) is not withdrawn via the membrane of the dialyzer. The stopping of the substituate pump with the simultaneous interruption of the withdrawal of fluid via the membrane of the dialyzer leads to a brief change in relative blood volume RBV(t) or hematocrit Hct(t). The change in blood volume RBV(t) can clearly be seen in FIG. 2 as a brief peak. Since the substitution pump is stopped at predetermined intervals during the blood treatment for a predetermined time interval, a large number of brief peaks of the blood volume results.

Figure 3:
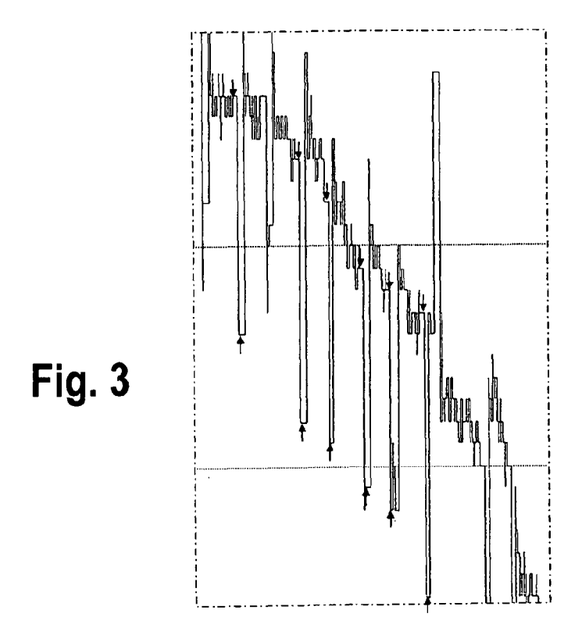
FIG. 3 shows an enlarged representation of the course of the relative blood volume as a function of time during a segment of the extracorporeal blood treatment.

FIG. 3 shows, in an enlarged representation, the brief changes in the blood volume as a result of stopping the substitution pump with the simultaneous interruption of the withdrawal of ultrafiltrate during a segment of the blood treatment. It can be seen that relative blood volume RBV(t) always diminishes by the same amount. The same applies to a quantity correlating with the blood volume, for example the hematocrit. After the switching-off of the substitution pump and interruption of the withdrawal of substituate, there is formed in the extracorporeal circuit a kind of thickened "blood column" which represents "a bolus", which leads to a change in blood volume RBV or the hematocrit.

The reduction in the relative blood volume or the increase in the density of the blood or a blood constituent is due in the case of postdilution to the fact that, immediately after the reduction in substitution rate $Q_S$ at which substitution fluid is fed to the blood and the simultaneous reduction in fluid rate $Q_{FM}$ at which fluid is withdrawn from the blood via the membrane of the dialyzer or filter, a corresponding quantity of fluid has still been withdrawn via the membrane from the blood now flowing out of the dialyzer, without a corresponding dilution with substitution fluid having taken place downstream of the dialyzer. As a result, the blood flowing out of the dialyzer or filter is thickened immediately after the reduction in rates $Q_S$ and $Q_{FM}$. A reduction in the quantity of the substitution fluid fed to the blood after the passage through the dialyzer (postdilution) therefore leads immediately to an increase in the density of the blood or the blood constituent in the blood circuit downstream of the dialyzer. If, on the contrary, rates $Q_S$ and $Q_{FM}$ are reduced in a predilution, the blood located in the dialyzer or filter has already been diluted by the previous supply of substitution fluid. Since the filtration in the dialyzer corresponding to the substituate flow is reduced or is absent, the density of the blood flowing back to the patient in this case diminishes, i.e. the relative blood volume increases.

Unit 19 for determining the relative blood volume determines the relative blood volume (RBV($t_1$)) before the stopping and the relative blood volume (RBV($t_2$)) after the stopping of the substitution pump and interruption of the withdrawal of ultrafiltrate. The time at which the supply of substitution fluid and the withdrawal of ultrafiltrate is interrupted does not coincide with time $t_1$ or $t_2$ at which the relative blood volume is measured. On the contrary, the measurement takes place at a time which lies in a specific time interval before or after the change in the aforementioned flow rates, because after the switching-off of the pumps it takes a certain amount of time until the "blood column" arrives at the measurement point. Fistula recirculation $R_A$ is then calculated on the basis of ratio k of the blood volume (RBV($t_2$))/(RBV($t_1$)) before and after the stopping of the substitution pump, as is described in detail below.

The individual quantities are denoted as follows:
$R_A$: recirculation in shunt/fistula
$Hct_P$: hematocrit of the dialysis patient
$Hct_A$: hematocrit in the arterial blood line between arterial needle and blood pump
$Hct_V$: hematocrit in the venous blood line between venous drip chamber and venous needle
BPR: delivery rate of the blood pump
UFR: net ultrafiltration rate
$Q_S$: delivery rate of the substitution pump
α: ratio of the UFR to the delivery rate of the blood pump
$β_1$: calculation factor with postdilution
$β_2$: calculation factor with predilution
RBV: relative blood volume
$Q_{FM}$: flow rate at which fluid is withdrawn from the blood via the membrane of the dialyzer
The following holds: $Q_{FM}=Q_S+UFR$ The case of postdilution will next be considered. It is assumed that blood pump 8 is pumping blood at delivery rate BPR through extracorporeal circuit 5A at time $t_1$, while substitution pump 16 is supplying substitution fluid at delivery rate $Q_S$ to the blood in the extracorporeal circuit downstream of blood chamber 3 of dialyzer 1 or the filter and fluid is being withdrawn at flow rate $Q_S$ via membrane 2 of the dialyzer.

$$Hct_A(t_1) = Hct_P(t_1) \cdot (1 - R_A(t_1)) + Hct_V(t_1) \cdot R_A(t_1) \tag{1}$$

$$Hct_V(t_1) = \frac{Hct_A(t_1)}{1 - \alpha} \tag{2}$$

$$\alpha = \frac{UFR(t_1)}{BPR(t_1)} \tag{3}$$

$$Hct_A(t_1) = Hct_P(t_1) \cdot (1 - R_A(t_1)) \cdot \frac{1 - \alpha}{1 - \alpha - R_A(t_1)} \tag{4}$$

It is now assumed that the substitution pump is stopped at time $t_2$ and at the same time the withdrawal of fluid via the membrane of the dialyzer is interrupted. Delivery rate BPR of the blood pump, on the other hand, remains unchanged (RBV($t_1$)=(RBV($t_2$)).

$$Hct_A(t_2) = Hct_P(t_2) \cdot (1 - R_A(t_2)) \cdot \frac{1 - \beta}{1 - \beta - R_A(t_2)} \tag{5}$$

$$\beta = \frac{UFR(t) + Q_S(t)}{BPR(t)} \tag{6}$$

The following results from equation (4) and (5):

$$\frac{Hct_A(t_1)}{Hct_A(t_2)} = \frac{(1 - \alpha) \cdot (1 - \beta - R_A(t_2))}{(1 - \beta) \cdot (1 - \alpha - R_A(t_1))} \cdot \frac{Hct_P(t_1) \cdot (1 - R_A(t_1))}{Hct_P(t_2) \cdot (1 - R_A(t_2))} \tag{7}$$

On the assumption that the patient's hematocrit and the recirculation do not change, i.e. $Hct_P(t_1)=Hct_P(t_2)=R(t_1)=R(t_2)=R$, the following results:

$$k = Hct_A(t_1)/Hct_A(t_2) = RBV(t_2)/RBV(t_1) < 1 \tag{8}$$

$$k = \frac{(1 - \alpha) \cdot (1 - \beta - R_A)}{(1 - \beta) \cdot (1 - \alpha - R_A)}$$

After transformation of equation (8), the following results:

$$R_A = \frac{(1-\alpha) \cdot (1-\beta) \cdot (1-k)}{(1-\alpha) - k \cdot (1-\beta)} \quad (9)$$

with $$\alpha = \frac{UFR(t)}{BPR(t)}$$

and $$\beta = \frac{UFR(t) + Q_S(t)}{BPR(t)}$$

In the case of predilution, the following results:

$$R_A = \frac{(1-\alpha) \cdot (1-\beta) \cdot (1-k)}{(1-\alpha) - k \cdot (1-\beta)} \quad (10)$$

with $$\alpha = \frac{UFR(t)}{BPR(t)} \quad (3)$$

and $$\beta = \frac{UFR(t) - Q_S(t)}{BPR(t)} \quad (11)$$

$$k = Hct_A(t_1)/Hct_A(t_2) = RBV(t_2)/RBV(t_1) > 1 \quad (12)$$

Evaluation unit 21 thus calculates the recirculation in the case of postdilution according to equation (9) and in the case of predilution according to equation (10) from ultrafiltration rate UFR and the delivery rate of the blood pump BPR and delivery rate $Q_S$ of the substitution pump as well as ratio k of hematocrit $Hct_A(t_1)$ and $Hct_A(t_2)$ of the blood in the arterial blood line measured by unit 19 at time $t_1$ before the interruption of the substitution and ultrafiltration and at time $t_2$ after the interruption of the substitution and ultrafiltration.

Instead of the hematocrit, coefficient k can also be calculated from the quotient of relative blood volume $RBV(t_2)$ at time $t_2$ after the interruption of the substitution and ultrafiltration and relative blood volume $RBV(t_1)$ at time $t_1$ before the interruption of the substitution and ultrafiltration. It is therefore solely a matter of the ratio of the relative blood volume before and after the interruption or of the ratio of a quantity correlating with the blood volume, for example the hematocrit.

In order to determine the share of fistula recirculation $R_A$ in total recirculation R, control unit 18 stops substitution pump 16 for a predetermined time interval ($Q_S=0$) and adjusts the delivery rates of dialyzing fluid pumps 13 and 14 in such a way that no fluid is withdrawn from the blood via the membrane of the dialyzer within the predetermined time interval ($Q_{FM}=0$). The effect of this is that the ultrafiltration is interrupted (UFR=0). The delivery rates of dialyzing fluid pumps 13 and 14 can also be adjusted equal to zero ($Q_{di}=Q_{do}=0$). Such a state arises, for example, when the dialyzer is bridged by a bypass as part of a pressure holding test. After the time interval has lapsed, control unit 18 readjusts the original delivery rates for the pumps.

Before and after the interruption of the substitution and the ultrafiltration, unit 19 determines relative blood volume RBV($t_1$) and RBV($t_2$) or hematocrit $Hct_A(t_1)$ and $Hct_A(t_2)$. Evaluation unit 21 calculates coefficient k from the values of the relative blood volume or the hematocrit. In addition, the evaluation unit calculates coefficient α according to equation (3) from net ultrafiltration rate UFR before the interruption of the substitution and ultrafiltration and the delivery rate of the blood pump BPR which remains constant before and after the interruption of the substitution and ultrafiltration. The computing unit calculates coefficient β according to equation (6) from net ultrafiltration rate UFR and substitution rate $Q_S$ and delivery rate BPR of the blood pump. Fistula recirculation $R_A$ is then calculated by the computing unit according to equation (9) in the case of postdilution.

In the case of predilution, the computing unit calculates coefficient α according to equation (3) and coefficient β according to equation (11). Fistula recirculation $R_A$ in the case of predilution is then calculated by the computing unit according to equation (10).

Since the measurement of the recirculation takes place very quickly, only fistula recirculation $R_A$, but not sum R of fistula and cardiopulmonary recirculation, is detected. Sum R of fistula recirculation $R_A$ and cardiopulmonary recirculation $R_{CP}$ is determined by unit 20 according to the known methods, for example according to the method known as thermodilution (EDTNA-ERCA Journal 19,6 (1993)).

Evaluation unit 21 then calculates the share of fistula recirculation $R_A$ in the sum R of fistula and cardiopulmonary recirculation. Cardiopulmonary recirculation $R_{CP}$ is calculated in the evaluation unit by the fact that the difference between measured sum R of fistula and cardiopulmonary recirculation and calculated fistula recirculation $R_A$ is determined.

The recirculation values can be displayed on a display unit (not shown) and/or be used to calculate other quantities characteristic of the extracorporeal blood treatment.

The invention claimed is:

1. A device for determining the share of fistula recirculation ($R_A$) or the share of cardiopulmonary recirculation ($R_{CP}$) in the total recirculation (R) for use with an apparatus for extracorporeal blood treatment, the extracorporeal blood treatment apparatus comprising: a dialyser or filter divided by a membrane into a first chamber and a second chamber, an extracorporeal blood circuit which includes the first chamber, a fluid system which includes the second chamber, a device for supplying blood at a specific blood flow rate $Q_B$ into the first chamber of the dialyser or filter, a substitution device for supplying substitution fluid at a specific substitution rate $Q_S$ to the extracorporeal blood circuit upstream or downstream of the dialyser or filter; and an ultrafiltration device for withdrawing fluid at a specific flow rate $Q_{FM}$ from the extracorporeal blood circuit via the membrane of the dialyser or filter;

the device for determining the share of fistula recirculation ($R_A$) or the share of cardiopulmonary recirculation ($R_{CP}$) in the total recirculation (R) comprising:

a control unit for controlling the substitution device and the ultrafiltration device, wherein the control unit is configured such that when substitution rate $Q_S$ is changed by a predetermined amount upstream or downstream of the dialyser or filter, the flow rate $Q_{FM}$ of the fluid withdrawn through the membrane is also changed;

a unit for determining the blood volume (RBV($t_1$)) and (RBV($t_2$)) or a quantity correlating with the blood volume before and after the change in the substitution rate and the flow rate of the fluid withdrawn through the membrane;

a unit for determining the total recirculation (R); and an evaluation unit configured to determine the fistula recirculation ($R_A$) from the ascertained blood volume or the quantity correlating with the blood volume before and after the change in substitution rate $Q_S$ and flow rate $Q_{FM}$, and configured to determine the share of the fistula recirculation ($R_A$) or the share of cardiopulmonary recirculation ($R_{CP}$) in the total recirculation (R) from the ascertained fistula recirculation ($R_A$) and the ascertained total recirculation (R).

2. The device according to claim 1, wherein the control unit is configured such that the substitution rate $Q_S$ and the flow rate $Q_{FM}$ are reduced by the same amount.

3. The device according to claim 1, wherein the control unit is configured such that the supply of substitution fluid and the withdrawal of fluid are interrupted.

4. The device according to claim 3, wherein the control unit is configured such that the supply of substitution fluid and the withdrawal of fluid are interrupted for a predetermined time interval.

5. The device according to claim 1,
wherein the substitution device of the extracorporeal blood treatment apparatus is configured such that the substitution fluid is provided to the extracorporeal blood circuit downstream of the first chamber, and fluid is withdrawn from the patient at a specific ultrafiltration rate UFR,
wherein the evaluation unit is configured such that the quotient of flow rate $Q_S$ and blood flow rate BPR is calculated as a first coefficient α, the quotient of the sum of ultrafiltration rate UFR and substitution rate $Q_S$, and blood flow rate BPR is calculated as a second coefficient β, and the fistula recirculation $R_A$ is determined on the basis of ratio k of blood volume RBV or the quantity correlating with the blood volume before and after the change in substitution rate $Q_S$ and flow rate $Q_{FM}$, and on the basis of first and second coefficients α, β.

6. The device according to claim 5, wherein the evaluation unit is configured such that fistula recirculation $R_A$ is calculated according to the following equation:

$$R_A = \frac{(1-\alpha)\cdot(1-\beta)\cdot(1-k)}{(1-\alpha)-k\cdot(1-\beta)}.$$

7. The device according to claim 1,
wherein the substitution device of the extracorporeal blood treatment apparatus is configured such that substitution fluid is provided to the extracorporeal blood circuit upstream of the first chamber, and fluid is withdrawn from the patient at a specific ultrafiltration rate UFR,
wherein the evaluation unit is configured such that the quotient of flow rate $Q_S$ and blood flow rate BPR is calculated as a first coefficient α, the quotient of the difference in ultrafiltration rate UFR and substitution rate $Q_S$ and blood flow rate BPR is calculated as a second coefficient β, and the fistula recirculation $R_A$ is determined on the basis of ratio k of blood volume RBV or the quantity correlating with the blood volume before and after the change in substitution rate $Q_S$ and flow rate $Q_{FM}$, and on the basis of first and second coefficients α, β.

8. The device according to claim 7, wherein the evaluation unit is configured such that fistula recirculation $R_A$ is calculated according to the following equation:

$$R_A = \frac{(1-\alpha)\cdot(1-\beta)\cdot(1-k)}{(1-\alpha)-k\cdot(1-\beta)}.$$

9. The device according to claim 1, wherein the evaluation unit is configured such that cardiopulmonary recirculation $R_{CP}$ is calculated from the difference in the ascertained total recirculation R and the ascertained fistula recirculation $R_A$.

10. A blood treatment apparatus and the device according to claim 1 for determining the share of fistula recirculation ($R_A$) or the share of cardiopulmonary recirculation ($R_{CP}$) in the total recirculation (R).

11. The blood treatment apparatus according to claim 10, wherein the blood treatment apparatus comprises:
a dialyser or filter, divided by a membrane into a first chamber and a second chamber;
an extracorporeal blood circuit that comprises a blood supply line leading to the first chamber and a blood discharge line leading away from the first chamber;
a fluid system which includes the second chamber of the dialyser or filter;
a substitution device with a first substituate line for supplying substitution fluid upstream of the dialyser or filter, said first substituate line leading to a first supply point on the blood supply line, and/or a second substituate line for supplying substitution fluid downstream of the dialyser or filter, said second substituate line leading to a second supply point on the blood discharge line; and
an ultrafiltration device, with which fluid can be withdrawn from the blood via the membrane of the dialyser.

* * * * *